United States Patent [19]

Tarrson et al.

[11] 4,011,658
[45] Mar. 15, 1977

[54] DEVICE FOR INSERTING DENTAL FLOSS THROUGH INTERPROXIMAL AREAS AND METHOD OF USING SAME

[75] Inventors: E. B. Tarrson, Chicago, Ill.; R. Young, Bowmanville, Canada

[73] Assignee: John O. Butler Company, Chicago, Ill.

[22] Filed: Oct. 20, 1975

[21] Appl. No.: 624,037

Related U.S. Application Data

[63] Continuation of Ser. No. 264,171, June 19, 1972, Pat. No. 3,929,144.

[52] U.S. Cl. ............................... 32/40 R; 132/93; 163/5; 223/99
[51] Int. Cl.² ....................................... A61C 15/00
[58] Field of Search .................. 163/1, 5; 223/99; 132/93; 32/40 R

[56] References Cited

UNITED STATES PATENTS

| 144,504 | 6/1915 | Schneider | 229/99 |
| 2,758,648 | 8/1956 | Dodds | 163/5 |
| 3,779,256 | 12/1973 | Maloney et al. | 132/93 |
| 3,838,801 | 10/1976 | David | 223/99 |
| 3,840,160 | 10/1976 | Pearce | 223/99 |

*Primary Examiner*—Robert Peshock
*Attorney, Agent, or Firm*—Laff, Whitesel & Rockman

[57] ABSTRACT

A device for inserting dental floss in difficult-to-reach areas under dental bridges or splints, comprising a length of flexible material formed into a loop, the ends of which are bonded together over a substantial portion to provide a stiffened elongated guide portion. The floss is threaded through the loop and the device, with the guide portion leading, is passed under two connected teeth of a bridge through interproximal areas whereby the floss is inserted through such areas.

7 Claims, 1 Drawing Figure

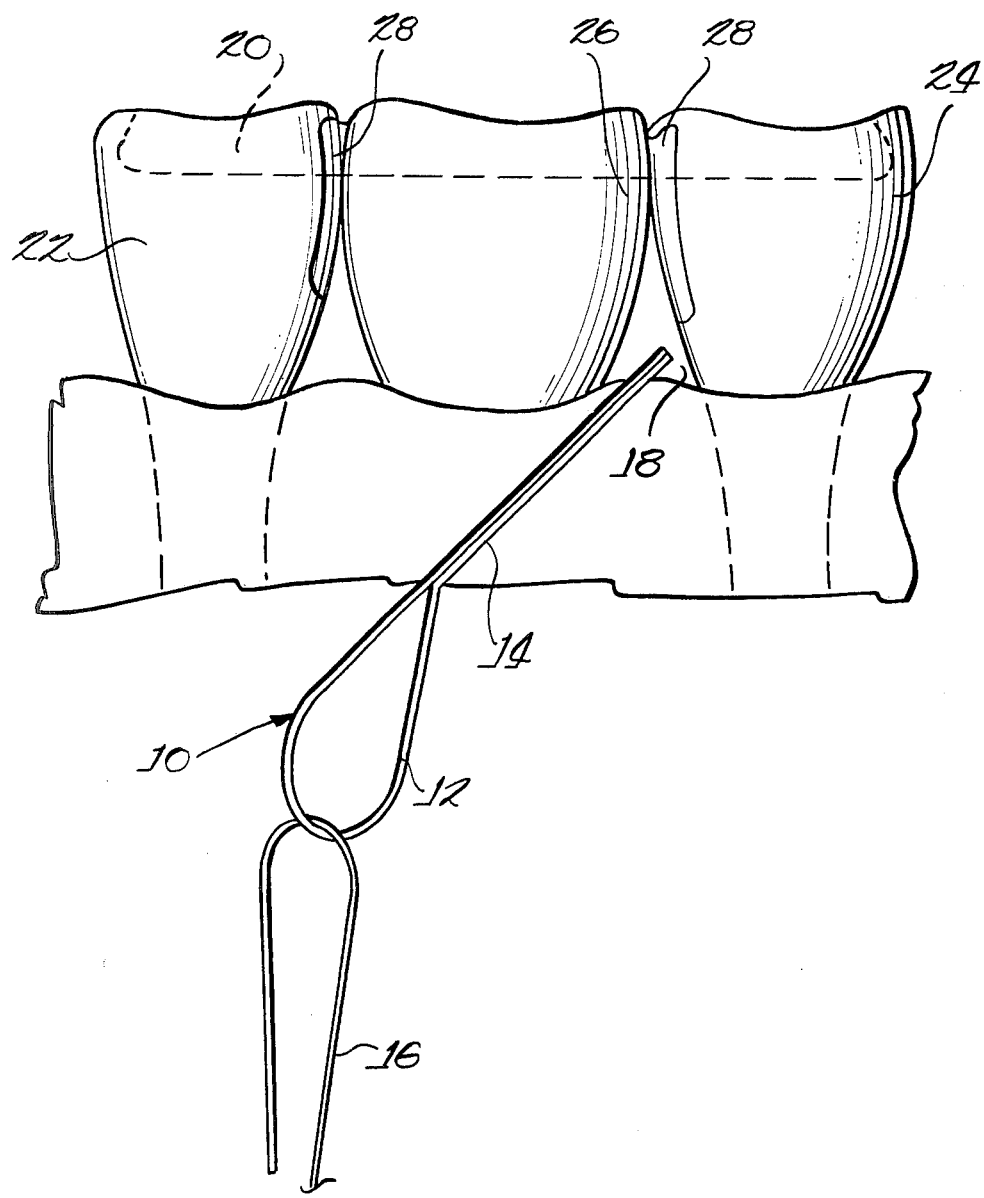

DEVICE FOR INSERTING DENTAL FLOSS THROUGH INTERPROXIMAL AREAS AND METHOD OF USING SAME

This is a continuation of application Ser. No. 264,171, filed June 19, 1972 and now U.S. Pat. No. 3,959,144 issued Dec. 30, 1975.

BACKGROUND OF THE INVENTION

This invention relates to a novel dental implement and more particularly to an article of manufacture useful for inserting dental floss in hard-to-reach areas between teeth and under fixed bridges or connecting caps. The relevant art includes dental implements and articles which are useful in cleaning teeth and fixed bridges.

The use of dental floss for oral hygiene is well known. Dental floss is a soft and flexible material which is usually manually inserted between teeth and worked toward the gum by a back and forth motion. It helps remove plaque and other debris and thus helps in cleaning the teeth. Insertion of floss is easily accomplished between normal teeth with normal spacing therebetween. However, where the user has a fixed dental bridge or connecting caps in place of natural teeth, the situation is different. In a fixed bridge, one or more artificial teeth or pontics are positioned in the place of missing teeth and are anchored to natural teeth by means of retainers, such as caps, crowns or jackets. The occlusal surfaces of the teeth forming the bridgework are bonded together to form a continuous surface from one end of the bridge to the other, so that a length of dental floss cannot be worked between two adjacent teeth of the bridge in a conventional manner. Instead, the floss must be inserted under the bridge. One implement heretofore used to insert floss under bridgework is shown in U.S. Pat. No. 2,522,794. This patent discloses the addition of a stiffening element made of fine wire to the end of the floss so as to present a needlelike structure. A disadvantage of this implement is the possibility of the wire causing injury to the gum tissue. Moreover, this device is more costly and more difficult to package and use than the present invention.

Accordingly, it is an object of this invention to provide a dental implement which may be used to position dental floss for cleaning under fixed bridges, splints, or connecting caps. It is another object to provide an economical means for removing plaque and otherwise cleaning the hard-to-reach areas under fixed bridges. Further objects will hereafter be apparent.

SUMMARY OF THE INVENTION

The invention in one form comprises a looped length of a relatively flexible strand-like material with the ends thereof bonded together to form an elongated portion having sufficient stiffness so that it can be inserted through spaces between the teeth. A length of dental floss is threaded through the looped end, the elongate end is pushed under a bridge and between a space between two teeth until the loop and floss are pulled through the space, and the floss is then separated from the loop. The floss remains in the space between the teeth and can now be used to clean the teeth.

BRIEF DESCRIPTION OF THE DRAWINGS

FIG. 1 is an enlarged perspective view of an embodiment of this invention which is being inserted with a length of floss threaded therethrough under a fixed bridge.

DESCRIPTION OF THE PREFERRED EMBODIMENT

Referring to FIG. 1 of the drawing, an embodiment 10 of the invention is shown. The device 10 is constructed of a relatively flexible strand-like or filamentary material, such as nylon sold under the trademark TYNEX. The device 10 consists of a looped portion 12 with the ends bonded together over a substantial length to form an elongated guide portion 14. Preferably, the entire length of guide portion 14 should be bonded or adhered together. Bonding or adhering may be accomplished by any suitable means, such as electronic welding. Because the elongated guide portion 14 consists of a double length of filament, it has greater rigidity than the looped portion 12.

The device 10 is employed by inserting a predetermined length of conventional dental floss 16 through the loop 12. Preferably about 18 inches of floss are used and about 4–5 inches of floss are inserted or pulled through the implement 10. The elongated guide portion 14 with connected floss is then introduced under a bridge 20, such as that shown in the drawing. The illustrated bridge 20 consists of two abutting teeth 22 and 24 and a pontic 26 intermediate the abutments 22 and 24. Solder joints or other attachments 28 interconnect the teeth. Because of the solder joint 28 between the teeth, floss cannot be introduced between them in the ordinary manner.

As shown in the drawing, the guide portion 14 is first inserted in the space 18 between the adjacent teeth 24 and 26, and then the implement 10 is passed all of the way through the space 18 until the attached floss 16 is completely pulled through the space. The floss 16 is thereafter removed from the device 10 and used in the conventional manner.

To facilitate use of the device 10, the guide portion 14 must be sufficiently rigid or stiffened so as to be capable of being inserted and drawn through the spaces between teeth, and the loop portion 12 must be sufficiently flexible so that it may be readily distorted when its passes between the teeth. The filament material TYNEX, referred to earlier, has been found to afford the proper properties for the device 10 and is capable of being electronically bonded. This material is sold commercially by E. I. duPont de Nemours and Co. The gauge or thickness of the filamentary material is preferably approximately 0.0012 inch. The overall length of the device 10 is approximately 3.5 inches with the looped portion 12 and the guide portion 14 being about equal in length.

With the use of the dental implement 10 of this invention, dental floss can be readily and easily positioned to clean normally spaced teeth, as well as fixed bridges, where difficulty is encountered when applying dental floss in a conventional manner. Since the filament from which the device 10 is formed is relatively durable and may be rinsed or otherwise cleaned, the device 10 can be used repeatedly with conventional dental floss. However, the device 10 is inexpensive, so that for hygienic reasons or otherwise, it may be disposed of after a single use. Inasmuch as the device 10 is formed of a relatively flexible material, appreciable damage to the teeth, gums and surrounding tissue will be avoided when it is employed.

While particular embodiments of the invention have been described, modifications may be made which fall within the true spirit and scope of the invention, and it is intended that these modifications be covered by the appended claims.

We claim:

1. A method of threading a long filament through an interstice comprising the steps of:
   a. forming a relatively large looped portion of soft and flexible material of fine diameter joined together to form a unitary elongated guide member adjacent to and integral with said loop, said material being soft and flexible enough to deform and fit through said interstice and thereafter springing back into the shape of the original large loop form;
   b. threading said long filament through said large looped portion;
   c. projecting said guide member through said interstice and pulling said guide until said loop and long filament pass completely through said interstice, whereby said loop may be relatively large to eliminate all threading problems and yet extremely flexible so that the loop may be deformed to be no larger in diameter than the interstice which it passes through, thereafter returning to its normal diameter; and
   d. removing said looped portion from its threaded association with said long filament.

2. The method of claim 1 wherein step (a) includes the added steps of forming said looped portion and guide member from a single and unitary plastic material part.

3. The method of claim 1 wherein said looped portion is formed large enough in diameter so that a person threading said long filament through said looped portion can place his fingers through said looped portion.

4. The method of claim 1 wherein said interstice is a space between a human tooth and an adjoining tooth or structure, said looped portion and guide member being formed with a maximum diameter which enables both the loop and the guide to pass entirely through said interstice, with said long filament threaded through said loop.

5. The method of claim 1 wherein step (a) includes the added steps of:
   (a-1) forming a discrete length of plastic filament,
   (a-2) looping said discrete length so that the ends of said length are substantially adjacent each other; and
   (a-3) bonding said ends of said discrete length together along a section thereof to form said elongated guide while leaving said discrete length of filament unbonded in said looped portion.

6. The method of claim 5 wherein said discrete length of plastic filament is a monofilament.

7. The method of claim 5 wherein the step (a-1) includes the added step of forming said discrete length of plastic as a nylon monofilament having a cross section in the order of 0.0024 inches.

* * * * *